US008674060B2

(12) United States Patent
Andersson

(10) Patent No.: US 8,674,060 B2
(45) Date of Patent: Mar. 18, 2014

(54) PEPTIDE LIGAND TO IMPAIR CANCER CELL MIGRATION

(75) Inventor: Tommy Andersson, Malmo (SE)

(73) Assignee: Wntresearch AB, Lund (SE)

( * ) Notice: Subject to any disclaimer, the term of this patent is extended or adjusted under 35 U.S.C. 154(b) by 789 days.

(21) Appl. No.: 11/946,303

(22) Filed: Nov. 28, 2007

(65) Prior Publication Data
US 2008/0207521 A1 Aug. 28, 2008

Related U.S. Application Data

(63) Continuation of application No. PCT/SE2006/000638, filed on May 30, 2006.

(30) Foreign Application Priority Data

May 30, 2005 (SE) ...................................... 0501204

(51) Int. Cl.
| C07K 7/04 | (2006.01) |
|---|---|
| C07K 7/06 | (2006.01) |
| C07K 7/08 | (2006.01) |
| A61K 38/08 | (2006.01) |
| A61K 38/10 | (2006.01) |

(52) U.S. Cl.
USPC ........... 530/300; 530/326; 530/327; 530/328; 530/329; 514/21.4; 514/21.5; 514/21.6; 514/21.7; 514/21.8

(58) Field of Classification Search
None
See application file for complete search history.

(56) References Cited

U.S. PATENT DOCUMENTS 8,497,352 B2 * 7/2013 Andersson ..................... 530/350
8,598,122 B2 * 12/2013 Blankesteijn et al. ....... 514/16.4

FOREIGN PATENT DOCUMENTS

| EP | 1033405 A2 * | 9/2000 |
|---|---|---|
| WO | 0031261 | 6/2000 |
| WO | 0132708 | 5/2001 |
| WO | WO 0132708 A1 * | 5/2001 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Safholm et al . (JBC 2006; 281: 2740-2749, IDS).*
Jonsson et al., "Repression of Wnt-5a impairs DDR1 phodphorylation and modifies adhesion and migration of mammary cells" Journal of Cell Science, 2001, vol. 114, pp. 2043-2053.
Deimek et al., "WNT-5 and G-protein signaling are required for collagen-induced DDR1 receptor activation and normal mammary Cell Adhesion" Int. J. Cancer, 2003, vol. 103, pp. 344-351.
Weeraratna et al., "WnT5a signaling directly affects cell motility and invasion of metastic melanoma" Cancer cell, Apr. 2002, vol. 1, pp. 279-288.
Kremenevskaja et al., "Wnt-5a has tumor suppressor activity in thyroid carcinoma" Oncogene, 2005, vol. 24, pp. 2144-2154.
Blanc et al., "Low expression of Wnt-5 a gene is associated with high-risk neuroblastoma" Oncogene, 2005, vol. 24, pp. 1277-1283.
Safholm et al., "A Formylated Hexapeptide Ligand Mimics the Ability of Wnt-5a to Impair Migration of Human Breast Epithelial Cells"; The Journal of Biological Chemistry; Feb. 3, 2006; vol. 28, No. 5; pp. 2740-2749.
EP Office Action relating to EP Application No. 06747832.1, mailed on Oct. 26, 2011.
EP Search Report relating to EP Application No. 11171215.4, mailed on Oct. 7, 2011.
Safholm et al., "The Wnt-5a-Derived Hexapeptide Foxy-5 Inhibits Breast Cancer Metastasis in vivo by Targeting Cell Motility" Clin Cancer Res 2008: 14 (20) Oct. 2008, www.aacrjournals.org, pp. 6556-6563, XP009109591.
English translation of JP Office Action issued in connection with JP Application No. 2008-514590, mailed on Oct. 31, 2011, pp. 1/4-4/4.
Derian et al., Selective Inhibition of N-Formylpeptide-Induced Neutrophil Activation by Carbamate-Modified Peptide Analogues, Biochemistry, 1996, pp. 1265-1269, vol. 35, issue 4, ACS Publications, Washington DC, USA.

* cited by examiner

Primary Examiner — Sheela J Huff
Assistant Examiner — Jessica H Roark
(74) Attorney, Agent, or Firm — Gesmer Updegrove LLP

(57) ABSTRACT

Loss of Wnt-5a protein expression in breast carcinoma patients is associated with a shorter recurrence-free survival as well as increased motility in mammary cell lines. Based on sequence analysis of Wnt-5a, peptide fragments were identified and investigated for their ability to mimic effects of the Wnt-5a protein on mammary cell adhesion and motility. Two of these peptides significantly increased adhesion and impaired the motility of non-tumorigenic breast cancer cell lines, both low in endogenous Wnt-5a protein expression. To identify the shortest possible peptide that still had an antimotile effect, sequential deletions of two amino acids from the N-terminal side of the shorter of these two peptides were performed. The effect on tumor cell adhesion was gradually lost, and when only 6 amino acids remained the effect was not detectable. However, formulation of the N-terminal methionine of this hexapeptide restored its effect on adhesion and reduced tumor cell motility. The formyl-Met-Asp-Gly-Cys-Glu-Leu (formylated SEQ ID NO: 15) peptide ligand can serve as a lead substance for anti-metastatic treatment in the 50% of human breast cancers where the endogenous expression of Wnt-5a is reduced.

13 Claims, 8 Drawing Sheets

SEQUENCE LISTING

```
<160> NUMBER OF SEQ ID NOS: 29

<210> SEQ ID NO 1
<211> LENGTH: 20
<212> TYPE: PRT
<213> ORGANISM: Homo sapiens

<400> SEQUENCE: 1

Leu Gly Thr Gln Gly Arg Leu Cys Asn Lys Thr Ser Glu Gly Met Asp
1               5                   10                  15

Gly Cys Glu Leu
            20

<210> SEQ ID NO 2
<211> LENGTH: 19
<212> TYPE: PRT
```

<213> ORGANISM: Homo sapiens

<400> SEQUENCE: 2

Gly Thr Gln Gly Arg Leu Cys Asn Lys Thr Ser Glu Gly Met Asp Gly
1               5                   10                  15

Cys Glu Leu

<210> SEQ ID NO 3
<211> LENGTH: 18
<212> TYPE: PRT
<213> ORGANISM: Homo sapiens

<400> SEQUENCE: 3

Thr Gln Gly Arg Leu Cys Asn Lys Thr Ser Glu Gly Met Asp Gly Cys
1               5                   10                  15

Glu Leu

<210> SEQ ID NO 4
<211> LENGTH: 17
<212> TYPE: PRT
<213> ORGANISM: Homo sapiens

<400> SEQUENCE: 4

Gln Gly Arg Leu Cys Asn Lys Thr Ser Glu Gly Met Asp Gly Cys Glu
1               5                   10                  15

Leu

<210> SEQ ID NO 5
<211> LENGTH: 16
<212> TYPE: PRT
<213> ORGANISM: Homo sapiens

<400> SEQUENCE: 5

Gly Arg Leu Cys Asn Lys Thr Ser Glu Gly Met Asp Gly Cys Glu Leu
1               5                   10                  15

<210> SEQ ID NO 6
<211> LENGTH: 15
<212> TYPE: PRT
<213> ORGANISM: Homo sapiens

<400> SEQUENCE: 6

Arg Leu Cys Asn Lys Thr Ser Glu Gly Met Asp Gly Cys Glu Leu
1               5                   10                  15

<210> SEQ ID NO 7
<211> LENGTH: 14
<212> TYPE: PRT
<213> ORGANISM: Homo sapiens

<400> SEQUENCE: 7

Leu Cys Asn Lys Thr Ser Glu Gly Met Asp Gly Cys Glu Leu
1               5                   10

<210> SEQ ID NO 8
<211> LENGTH: 13
<212> TYPE: PRT
<213> ORGANISM: Homo sapiens

<400> SEQUENCE: 8

Cys Asn Lys Thr Ser Glu Gly Met Asp Gly Cys Glu Leu
1               5                   10

```
<210> SEQ ID NO 9
<211> LENGTH: 12
<212> TYPE: PRT
<213> ORGANISM: Homo sapiens

<400> SEQUENCE: 9

Asn Lys Thr Ser Glu Gly Met Asp Gly Cys Glu Leu
1               5                   10

<210> SEQ ID NO 10
<211> LENGTH: 11
<212> TYPE: PRT
<213> ORGANISM: Homo sapiens

<400> SEQUENCE: 10

Lys Thr Ser Glu Gly Met Asp Gly Cys Glu Leu
1               5                   10

<210> SEQ ID NO 11
<211> LENGTH: 10
<212> TYPE: PRT
<213> ORGANISM: Homo sapiens

<400> SEQUENCE: 11

Thr Ser Glu Gly Met Asp Gly Cys Glu Leu
1               5                   10

<210> SEQ ID NO 12
<211> LENGTH: 9
<212> TYPE: PRT
<213> ORGANISM: Homo sapiens

<400> SEQUENCE: 12

Ser Glu Gly Met Asp Gly Cys Glu Leu
1               5

<210> SEQ ID NO 13
<211> LENGTH: 8
<212> TYPE: PRT
<213> ORGANISM: Homo sapiens

<400> SEQUENCE: 13

Glu Gly Met Asp Gly Cys Glu Leu
1               5

<210> SEQ ID NO 14
<211> LENGTH: 7
<212> TYPE: PRT
<213> ORGANISM: Homo sapiens

<400> SEQUENCE: 14

Gly Met Asp Gly Cys Glu Leu
1               5

<210> SEQ ID NO 15
<211> LENGTH: 6
<212> TYPE: PRT
<213> ORGANISM: Homo sapiens

<400> SEQUENCE: 15

Met Asp Gly Cys Glu Leu
1               5

<210> SEQ ID NO 16
<211> LENGTH: 15
<212> TYPE: PRT
```

-continued

<213> ORGANISM: Homo sapiens

<400> SEQUENCE: 16

Ser Arg Ala Ala Arg Pro Lys Asp Leu Pro Arg Asp Trp Leu Trp
1               5                   10                  15

<210> SEQ ID NO 17
<211> LENGTH: 15
<212> TYPE: PRT
<213> ORGANISM: Homo sapiens

<400> SEQUENCE: 17

Asp Ala Arg Glu Arg Glu Arg Ile His Ala Lys Gly Ser Tyr Glu
1               5                   10                  15

<210> SEQ ID NO 18
<211> LENGTH: 15
<212> TYPE: PRT
<213> ORGANISM: Homo sapiens

<400> SEQUENCE: 18

Ala Asp Phe Arg Lys Val Gly Asp Ala Leu Lys Glu Lys Tyr Asp
1               5                   10                  15

<210> SEQ ID NO 19
<211> LENGTH: 15
<212> TYPE: PRT
<213> ORGANISM: Homo sapiens

<400> SEQUENCE: 19

Val Lys Ala Lys Lys Ala Thr Glu Ile Val Asp Gln Phe Val Ala
1               5                   10                  15

<210> SEQ ID NO 20
<211> LENGTH: 13
<212> TYPE: PRT
<213> ORGANISM: Homo sapiens

<400> SEQUENCE: 20

Ser Gln Leu Ala Gly Leu Ser Gln Gly Gln Lys Lys Leu
1               5                   10

<210> SEQ ID NO 21
<211> LENGTH: 13
<212> TYPE: PRT
<213> ORGANISM: Homo sapiens

<400> SEQUENCE: 21

Gly Asp Asn Ile Asp Tyr Gly Tyr Arg Phe Ala Lys Glu
1               5                   10

<210> SEQ ID NO 22
<211> LENGTH: 13
<212> TYPE: PRT
<213> ORGANISM: Homo sapiens

<400> SEQUENCE: 22

Arg Gly Tyr Asp Gln Phe Lys Thr Val Gln Thr Glu Arg
1               5                   10

<210> SEQ ID NO 23
<211> LENGTH: 10
<212> TYPE: PRT
<213> ORGANISM: Homo sapiens

<400> SEQUENCE: 23

```
Tyr Gln Asp His Met Gln Tyr Ile Gly Glu
1               5                   10
```

<210> SEQ ID NO 24
<211> LENGTH: 10
<212> TYPE: PRT
<213> ORGANISM: Homo sapiens

<400> SEQUENCE: 24

```
Gln Tyr Gln Phe Arg His Arg Arg Trp Asn
1               5                   10
```

<210> SEQ ID NO 25
<211> LENGTH: 10
<212> TYPE: PRT
<213> ORGANISM: Homo sapiens

<400> SEQUENCE: 25

```
Arg Val Met Gln Ile Gly Ser Arg Glu Thr
1               5                   10
```

<210> SEQ ID NO 26
<211> LENGTH: 8
<212> TYPE: PRT
<213> ORGANISM: Homo sapiens

<400> SEQUENCE: 26

```
His Asn Asn Glu Ala Gly Arg Arg
1               5
```

<210> SEQ ID NO 27
<211> LENGTH: 8
<212> TYPE: PRT
<213> ORGANISM: Homo sapiens

<400> SEQUENCE: 27

```
Asn Ser Arg Gly Lys Leu Val Gln
1               5
```

<210> SEQ ID NO 28
<211> LENGTH: 21
<212> TYPE: PRT
<213> ORGANISM: Homo sapiens

<400> SEQUENCE: 28

```
Cys Pro Ile Leu Lys Glu Ser His Pro Leu Tyr Asn Lys Val Arg Thr
1               5                   10                  15

Gly Gln Val Pro Asn
            20
```

<210> SEQ ID NO 29
<211> LENGTH: 19
<212> TYPE: PRT
<213> ORGANISM: Homo sapiens

<400> SEQUENCE: 29

```
Cys Pro Arg Val Leu Lys Pro Ser Tyr Leu Ser Tyr Lys Phe Leu Gly
1               5                   10                  15

Glu Arg Asp
```

PEPTIDE LIGAND TO IMPAIR CANCER CELL MIGRATION

PRIORITY INFORMATION

The present application is a continuation of PCT Application Serial No. PCT/SE2006/000638 filed on May 30, 2006 that claims priority to Swedish Application Serial No. SE-0501204-2, filed on May 30, 2005. Both applications are incorporated herein by reference in their entireties.

BACKGROUND OF THE INVENTION

1. Field of the Invention

The present invention relates to a novel peptide ligand i.a., to be used to impair cancer cell migration, in particular breast and colon cancer, and to act as a tumour suppressor in thyroid carcinoma and neurocarcinoma, In particular it relates to a hexapeptide ligand.

2. Brief Description of the Art

The Wnt proteins are a family of secreted glyco-proteins with a molecular weight of 39-46 kDa that participate in development and tumourigenesis via autocrine or paracrine routes (for review see (1-3)). Secreted Wnt proteins bind to and activate G-protein-coupled receptors of the Frizzled (Frz) family (4, 5). The LDL-receptor related proteins LRP5 or LRP6 are presumed to act as co-receptors in this context (6, 7). Based on the ability of different Wnt proteins to transform mouse mammary epithelial cells, thy can be divided into three different classes. Wnt-1, -3a, and -7a have the greatest transforming capacity; Wnt-2, -5b, and -7b have an intermediate transforming capacity; and Wnt-4, -5a, and -6 are non-transforming (8).

It has previously been reported that a low-level of Wnt-5a protein expression in a primary invasive breast carcinoma is associated with higher histological grade (poor differentiation) and a shortened recurrence-free survival due to a more rapid development of distant metastases (9). This association is not due to an effect of Wnt-5a on proliferation, since no correlation between loss of Wnt-5a protein expression and the proliferative marker Ki67 has been detected (9). The only presently available explanation for how the presence of Wnt-5a can reduce the metastatic capacity of invasive breast cancer is its ability to enable increased adhesion, presumably via the collagen-activated discoidin domain receptor 1 (DDR1), however it is possible that as yet undefined mechanisms could also contribute to the described clinical effect of Wnt-5a on tumour progression. Despite this, a Wnt-5a-dependent activation of DDR1 results in decreased motility and invasive potential of breast epithelial cancer cells (10). In breast epithelial cells that are normally firmly adhesive, a decreased expression of Wnt-5a and thus a decreased adhesion will increase their motility. In accordance, it has been observed that by stably introducing a Wnt-5a expression vector into a MCF-7 breast cancer cell line low in endogenous expression of Wnt-5a, was required for collagen-induced activation of the adhesion receptor DDR1 (10). In concordance, transfection of the normal human mammary epithelial cell line HB2 (11) stably transfected with Wnt-5a or antisense Wnt-5a caused a respective increased or decreased adhesion of these cells to collagen I (12). In human mammary cells it is not yet established via which of the different Frz-receptors that Wnt-5a mediates its effects. However, in both fibroblast-like synoviocytcs and in malignant melanoma cells it has been clearly shown with a specific blocking Ab that the receptor responsible for the Wnt-5a-induced effects is Frz-5 (13, 14).

To develop a specific treatment for breast cancer metastasis based on the functional role of Wnt-5a it is important to understand the cellular and molecular events responsible for its effects on this epithelial tumour. One of the critical and initial events in cancer metastasis is the ability of the transformed cells to de-adhere from each other and also from ECM components of the basement membrane (15). In the presence of Wnt-5a, the adhesion receptor DDR1 receptor can be activated by collagen in breast epithelial cells and is therefore a likely candidate that could mediate the Wnt-5a-induced increased adhesion of these cells to collagen (10). A possible explanation for the elevated metastatic activity seen in Wnt-5a lacking breast carcinomas could be a reduced adhesion and a subsequent increased motile activity In these tumour cells. One approach to reduce the metastatic activity in breast carcinomas lacking Wnt-5a protein expression could therefore be to find a way to overcome the translational defect responsible for the loss of Wnt-5a protein expression (16) and another to reconstitute the Wnt-5a-induced activation of the cells. Experimentally, addition of recombinant Wnt-5a to differentiated thyroid carcinomas has been shown to have tumour suppressor activity (17). However, addition of a large 43 kDa Wnt-5a protein to a patient, most likely over an extended period of time, does not emerge as a very attractive approach.

Previous work in platelets by Andersen and co-workers (18) has identified two different hexapeptide fragments that specifically can activate the G-protein-coupled protease-activated receptors PAR1 and PAR4, respectively. Other well-studied small peptides that can specifically bind and activate G-protein-coupled receptors on mammalian cells with high potency are the bacterial derived formylated peptides that bind to and activate the chemotactic peptide receptor on leukocytes (19). In this situation the formyl group has been shown to profoundly increase the binding affinities for the peptides to the receptor and consequently also for amplifying the activation of the cells (19). Interestingly enough, these peptides are functionally active even at a low pH such as that encountered at sites of inflammation. The pH at inflammatory sites is most likely lower than the estimated pH in a solid tumour (20, 21).

SUMMARY OF THE PRESENT INVENTION

The present invention relates to novel peptide ligands, in particular hexapeptide ligand derivatives of Wnt-5a showing reduced motility to cancer cells, and increased adhesion, thereby to impair cancer cell migration. In the present study 14 peptide fragments, based on sequence analysis of Wnt-5a, for their ability to mimic the effects of the Wnt-5a protein on mammary cell adhesion and locomotion have been identified and investigated in order to identify a potential substance for anti-metastatic treatment of breast and colon carcinomas having a reduced endogenous expression of Wnt5a. The peptide ligands will also act as a tumour suppressor in thyroid carcinoma and neurocarcinoma, In particular the invention relates to a hexapeptide ligand.

DETAILED DESCRIPTION OF THE PRESENT INVENTION

Figure 1:
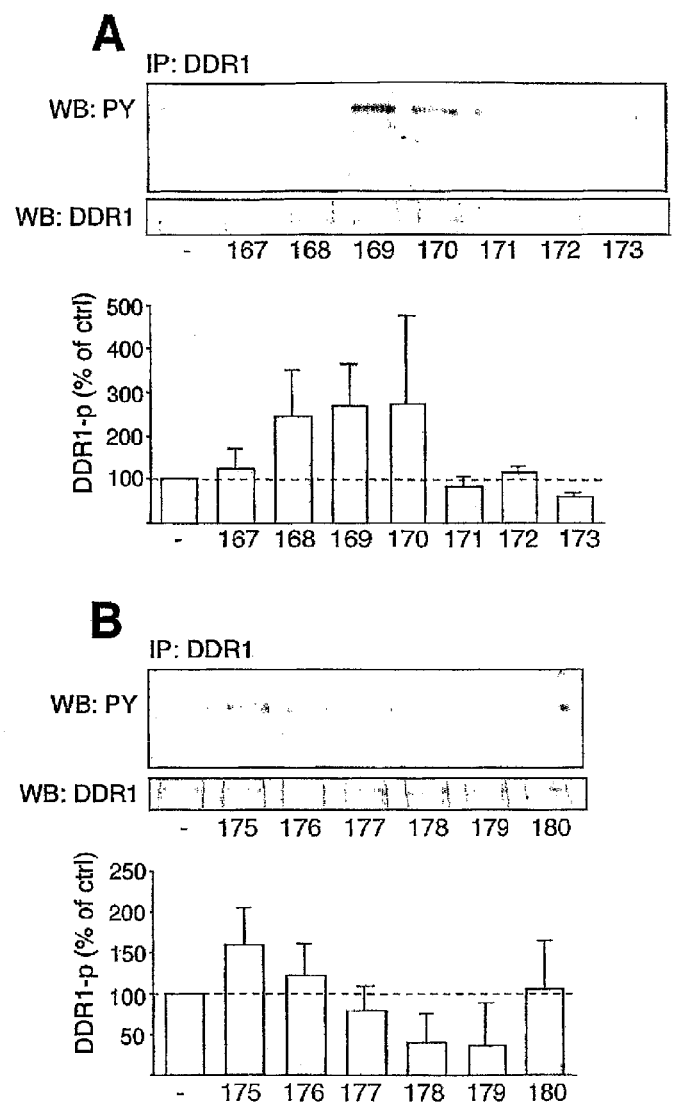
FIGS. 1A and 1B illustrate the effects of crude peptides on collagen-induced DDR1 phosphorylation in Wnt-5a anti-sense HB2 cells.

The invention will be discussed and clarified in the following with reference to the technical description below as well as the accompanying figures and graphs showing details of tests carried out.

The present invention relates to novel peptide structures having the amino acid sequences:

```
LGTQGRLCNKTSEGMDGCEL    (SEQ ID NO: 1)
GTQGRLCNKTSEGMDGCEL     (SEQ ID NO: 2)
TQGRLCNKTSEGMDGCEL      (SEQ ID NO: 3)
QGRLCNKTSEGMDGCEL       (SEQ ID NO: 4)
GRLCNKTSEGMDGCEL        (SEQ ID NO: 5)
RLCNKTSEGMDGCEL         (SEQ ID NO: 6)
LCNKTSEGMDGCEL          (SEQ ID NO: 7)
CNKTSEGMDGCEL           (SEQ ID NO: 8)
NKTSEGMDGCEL            (SEQ ID NO: 9)
KTSEGMDGCEL             (SEQ ID NO: 10)
TSEGMDGCEL              (SEQ ID NO: 11)
SEGMDGCEL               (SEQ ID NO: 12)
EGMDGCEL                (SEQ ID NO: 13)
GMDGCEL                 (SEQ ID NO: 14)
MDGCEL                  (SEQ ID NO: 15)
``` or a formylated derivative thereof.

In a preferred embodiment of the invention it relates to the peptide structures of SEQ ID NO: 9 to SEQ ID NO: 15 or a formylated derivative thereof.

In particular the invention relates to SEQ ID NO: 15 or a formylated derivative thereof.

In a further aspect of the invention it relates to the use of one or more of the amino acids encoded by the sequences:

```
LGTQGRLCNKTSEGMDGCEL    (SEQ ID NO: 1)
GTQGRLCNKTSEGMDGCEL     (SEQ ID NO: 2)
TQGRLCNKTSEGMDGCEL      (SEQ ID NO: 3)
QGRLCNKTSEGMDGCEL       (SEQ ID NO: 4)
GRLCNKTSEGMDGCEL        (SEQ ID NO: 5)
RLCNKTSEGMDGCEL         (SEQ ID NO: 6)
LCNKTSEGMDGCEL          (SEQ ID NO: 7)
CNKTSEGMDGCEL           (SEQ ID NO: 8)
NKTSEGMDGCEL            (SEQ ID NO: 9)
KTSEGMDGCEL             (SEQ ID NO: 10)
TSEGMDGCEL              (SEQ ID NO: 11)
SEGMDGCEL               (SEQ ID NO: 12)
EGMDGCEL                (SEQ ID NO: 13)
GMDGCEL                 (SEQ ID NO: 14)
MDGCEL                  (SEQ ID NO: 15)
``` or a formylated derivative thereof in the manufacture of a pharmaceutical composition used in the treatment of cancer by impairing cancer cell motility, in particular the amino acids are selected from the group of:

```
NKTSEGMDGCEL            (SEQ ID NO: 9)
KTSEGMDGCEL             (SEQ ID NO: 10)
TSEGMDGCEL              (SEQ ID NO: 11)
SEGMDGCEL               (SEQ ID NO: 12)
EGMDGCEL                (SEQ ID NO: 13)
GMDGCEL                 (SEQ ID NO: 14)
MDGCEL                  (SEQ ID NO: 15)
``` or a formylated derivative thereof.

In a still further aspect of the invention it relates to a pharmaceutical composition containing a therapeutically active amount of one or more cancer cell motility impairing active peptide sequences selected from the group consisting of:

```
LGTQGRLCNKTSEGMDGCEL    (SEQ ID NO: 1)
GTQGRLCNKTSEGMDGCEL     (SEQ ID NO: 2)
TQGRLCNKTSEGMDGCEL      (SEQ ID NO: 3)
QGRLCNKTSEGMDGCEL       (SEQ ID NO: 4)
GRLCNKTSEGMDGCEL        (SEQ ID NO: 5)
RLCNKTSEGMDGCEL         (SEQ ID NO: 6)
LCNKTSEGMDGCEL          (SEQ ID NO: 7)
CNKTSEGMDGCEL           (SEQ ID NO: 8)
NKTSEGMDGCEL            (SEQ ID NO: 9)
KTSEGMDGCEL             (SEQ ID NO: 10)
TSEGMDGCEL              (SEQ ID NO: 11)
SEGMDGCEL               (SEQ ID NO: 12)
```

```
EGMDGCEL              (SEQ ID NO: 13)

GMDGCEL               (SEQ ID NO: 14)

MDGCEL                (SEQ ID NO: 15)
``` or a formylated derivative thereof, optionally in combination with an inert carrier or excipient,
in particular the active peptide is selected from the group consisting of:

```
NKTSEGMDGCEL          (SEQ ID NO: 9)

KTSEGMDGCEL           (SEQ ID NO: 10)

TSEGMDGCEL            (SEQ ID NO: 11)

SEGMDGCEL             (SEQ ID NO: 12)

EGMDGCEL              (SEQ ID NO: 13)

GMDGCEL               (SEQ ID NO: 14)

MDGCEL                (SEQ ID NO: 15)
``` or a formylated derivative thereof, more particularly the active peptide is

```
MDGCEL                (SEQ ID NO: 15)
``` or a formylated derivative thereof.

In a further aspect of the present invention it relates to a method for impairing cancer cell motility in human, in particular in humans suffering from breast cancer, by administering a therapeutically effective amount of one or more of the peptide sequences selected from the group consisting of:

```
LGTQGRLCNKTSEGMDGCEL  (SEQ ID NO: 1)

GTQGRLCNKTSEGMDGCEL   (SEQ ID NO: 2)

TQGRLCNKTSEGMDGCEL    (SEQ ID NO: 3)

QGRLCMKTSEGMDGCEL     (SEQ ID NO: 4)

GRLCNKTSEGMDGCEL      (SEQ ID NO: 5)

RLCNKTSEGMDGCEL       (SEQ ID NO: 6)

LCNKTSEGMDGCEL        (SEQ ID NO: 7)

CNKTSEGMDGCEL         (SEQ ID NO: 8)

NKTSEGMDGCEL          (SEQ ID NO: 9)

KTSEGMDGCEL           (SEQ ID NO: 10)

TSEGMDGCEL            (SEQ ID NO: 11)

SEGMDGCEL             (SEQ ID NO: 12)

EGMDGCEL              (SEQ ID NO: 13)

GMDGCEL               (SEQ ID NO: 14)

MDGCEL                (SEQ ID NO: 15)
``` or a formylated derivative thereof.

In the following some abbreviations have been used, these are
CM, Wnt-5a-conditioned media;
DDR1, discoidin domain receptor 1;
F-actin, filamentous actin;
Frz, Frizzled;
MTS, (3-(4,5-dimethylthiazol-2-yl)-5-(3-carboxymethoxyphenyl)-2-(4-sulfophenyl)-2H-tetrazolium, inner salt;
PP1, 4-amino-5-(4-methyl-phenyl)-7-(t-butyl)pyrozolo-D-3,4-pyrimidine.

Results

Figure 2:
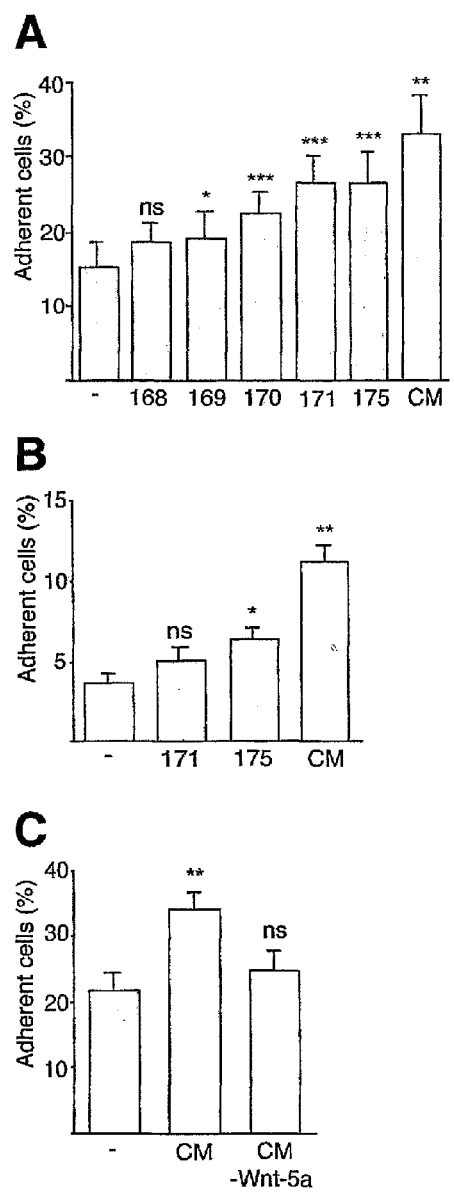
FIGS. 2A-2C illustrate the effects of crude peptides on adhesion of Wnt-5a antisense HB2 cells to collagen.

Peptide-induced effects on adhesion and migration of Wnt-5a antisense HB2 cells. Table 1 lists the initial 14-peptide fragments that were derived from the Wnt-5a sequence and investigated for their ability to mimic the effects of the Wnt-5a protein on mammary cell adhesion and motility. Previous studies have shown that the presence of Wnt-5a protein is required for collagen-induced activation of the adhesion receptor DDR1 and for maximal adhesion of mammary cells to collagen (12). Therefore, DDR1 phosphorylation and adhesion was used as screening parameters for the ability of the different peptides to mimic Wnt-5a-mediated effects in Wnt-5a antisense HB2 cells. These cells were chosen since their very low level of Wnt-5a makes it easier to see a Wnt-5a-dependent effect of the peptides. As shown from the representative blots and the accumulated densitometric analysis, peptides numbered 168, 169, 170 and 175 (100 caused a significant DDR1 phosphorylation. The purity of these peptides was in the initial screens (FIGS. 1 and 2) approximately 65% as determined by HPLC analysis (data not shown). The percentage of adhering cells to collagen I in the presence of the four peptides (168, 169, 170, and 175) was next determined that in FIG. 1 enabled phosphorylation of DDR1. Peptide 171 was included as a negative control and Wnt-5a conditioned media (CM) as a positive control. The results show that peptide 168 did not have any effect on adhesion whereas the presumed negative control peptide had a significant effect on adhesion (FIG. 2A). The fact that no DDR1 phosphorylation in the presence of peptide 171 (FIG. 1A) was observed, made it logical to suspect that the mechanism whereby peptide 171 affects adhesion is independent of DDR1. Since DDR1 activation is independent of $\beta_1$-integrins (22) and that Wnt-5a-dependent mammary cell adhesion is insensitive to pre-incubation with an anti-β1-integrin Ab (12), suspended HB2 cells were pre-treated with a blocking monoclonal anti-β1-integrin Ab for 45 min at 37° C. The results revealed that the increased adhesion caused by the control peptide, 171, is most likely $\beta_1$-integrin-dependent (FIG. 2B). These effects were in contrast to that of peptide 175 (FIG. 2B). In this context it should be pointed out that none of these 65% pure peptides increased HB2 cell adhesion to the extent of the CM (FIG. 2A). To ascertain that the effects of CM in FIG. 2 were mediated by Wnt-5a, experiments were performed in which the CM had been pretreated with a Wnt-5a Ab and protein A and by these mean depleted of Wnt5a. These control experiments reveal that CM depleted of Wnt-5a had no effect on adhesion (FIG. 2C).

TABLE 1

The peptide sequences and the position they correspond to in the Wnt-5a protein

| Peptide | Amino acid sequence | SEQ ID NO | Position in the Wnt-5a sequence | No. of amino acids |
|---|---|---|---|---|
| 167 | SRAARPKDLPRDWLW | SEQ ID NO.: 16 | aa 150-164 | 15 |
| 168 | DARERERIHAKGSYE | SEQ ID NO.: 17 | aa 183-197 | 15 |
| 169 | ADFRKVGDALKEKYD | SEQ ID NO.: 18 | aa 242-256 | 15 |
| 170[A] | VKAKKATEIVDQFVA | SEQ ID NO.: 19 | aa 350-364 | 15 |

TABLE 1-continued

The peptide sequences and the position they correspond to in the Wnt-5a protein

| Peptide | Amino acid sequence | SEQ ID NO | Position in the Wnt-5a sequence | No. of amino acids |
|---|---|---|---|---|
| 171 | SQLAGLSQGQKKL | SEQ ID NO.: 20 | aa 55-67 | 13 |
| 172 | GDNIDYGYRFAKE | SEQ ID NO.: 21 | aa 168-180 | 13 |
| 173 | RGYDQFKTVQTER | SEQ ID NO.: 22 | aa 327-339 | 13 |
| 174[B] | LGTQGRLCNKTSEGMDGCEL | SEQ ID NO.: 1 | aa 303-322 | 20 |
| 175 | NKTSEGMDGCEL | SEQ ID NO.: 9 | aa 311-322 | 12 |
| 176 | YQDHMQYIGE | SEQ ID NO.: 23 | aa 71-80 | 10 |
| 177 | QYQFRHRRWN | SEQ ID NO.: 24 | aa 90-99 | 10 |
| 178 | RVMQIGSRET | SEQ ID NO.: 25 | aa 111-120 | 10 |
| 179 | HNNEAGRR | SEQ ID NO.: 26 | aa 206-213 | 8 |
| 180 | NSRGKLVQ | SEQ ID NO.: 27 | aa 264-271 | 8 |

[A]The 3 cysteines in the Wnt-5a sequence were exchanged to alanines (A) in the peptide
[B]Extended sequence based on peptide 175

Figure 3:
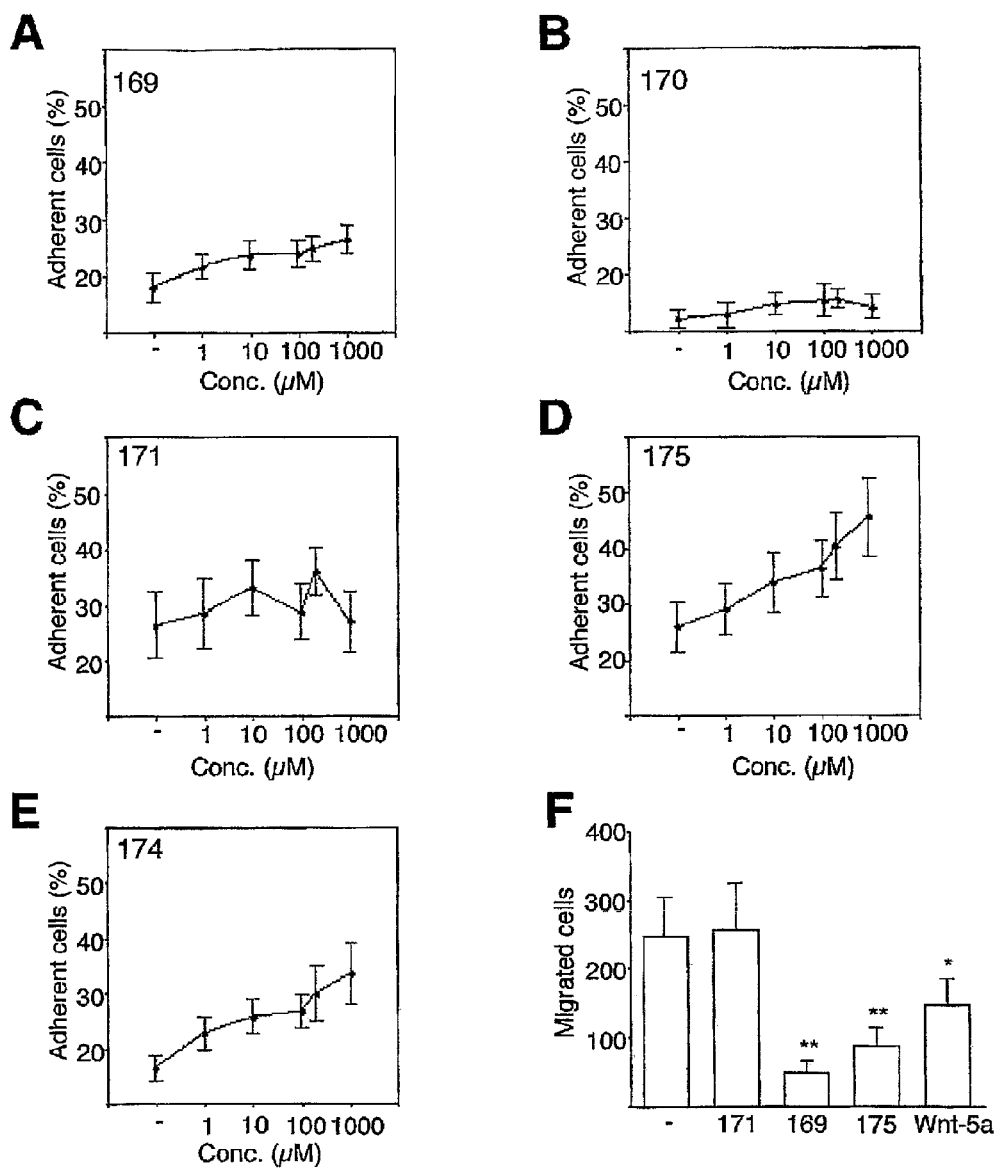
FIGS. 3A-3F illustrate the effects of the selected and pure peptides on the ability of Wnt-5a antisense HB2 cells to adhere and migrate.

Having identified four peptide fragments from the Wnt-5a protein with capacities to increase adhesion of HB2 cells having a low endogenous Wnt-5a expression (FIG. 2A), a concentration-dependent analysis of these peptides were next made but now at a higher purity (95% as determined by HPLC). Clearly, the 175 peptide was most effective in increasing HB2 cell adhesion to collagen I (FIG. 3A-3D). The effect of peptide 169 increased when tested at higher purity, whereas the effects of peptides 170 and 171 at this higher purity were lost or less consistent. Addition of the 95% pure peptides 169 and 175 at the same time did not further increase the adhesion of HB2 cells in comparison with the peptide 175 alone (data not shown). It has previously been suggested, based on a theoretical reasoning, that the active part of the Wnt-5b molecule is 20 amino acids long. Interestingly enough, the present peptide 175 is contained within the corresponding domain within the Wnt-5a molecule. Therefore the thought if the efficiency of a peptide 175 further comprising the missing 8 amino acids in order to have a peptide that perfectly corresponds to the previously suggested active site of the Wnt-5a protein on cell adhesion could be improved, was examined. Clearly, the 20 amino acids long peptide 174 (Table 1) was not as effective as the shorter peptide 175 in increasing the adhesion of HB2 cells to collagen I (FIG. 3E).

Increasing Wnt-5a protein levels in HB2 cells has been shown to impair HGF-induced migration in a collagen gel, presumably due to increased adhesion to the collagen (10). Due to the presently observed effect of peptides 169 and 175 on cell adhesion it was next investigated the effects of these peptides (95% pure) on migration of Wnt-5a low HB2 cells. As described in the methods section, the cells were allowed to migrate in a modified Boyden chamber for 18 h in the presence or absence of the 95% pure peptides 169 or 175 (100 µM). As positive and negative controls respectively, purified recombinant Wnt-5a (0.4 µg/ml) or the 95% pure peptide 171 (100 µM) were added. Both peptide 169 and 175 as well as the recombinant Wnt-5a effectively decreased the migration of Wnt-5a antisense HB2 cells (FIG. 3F). The control peptide 171 had no effect on migration (FIG. 3F).

Peptide-induced effects on adhesion and migration of Wnt-5a-deficient MDA-MB-468 tumour cells.

Figure 4:
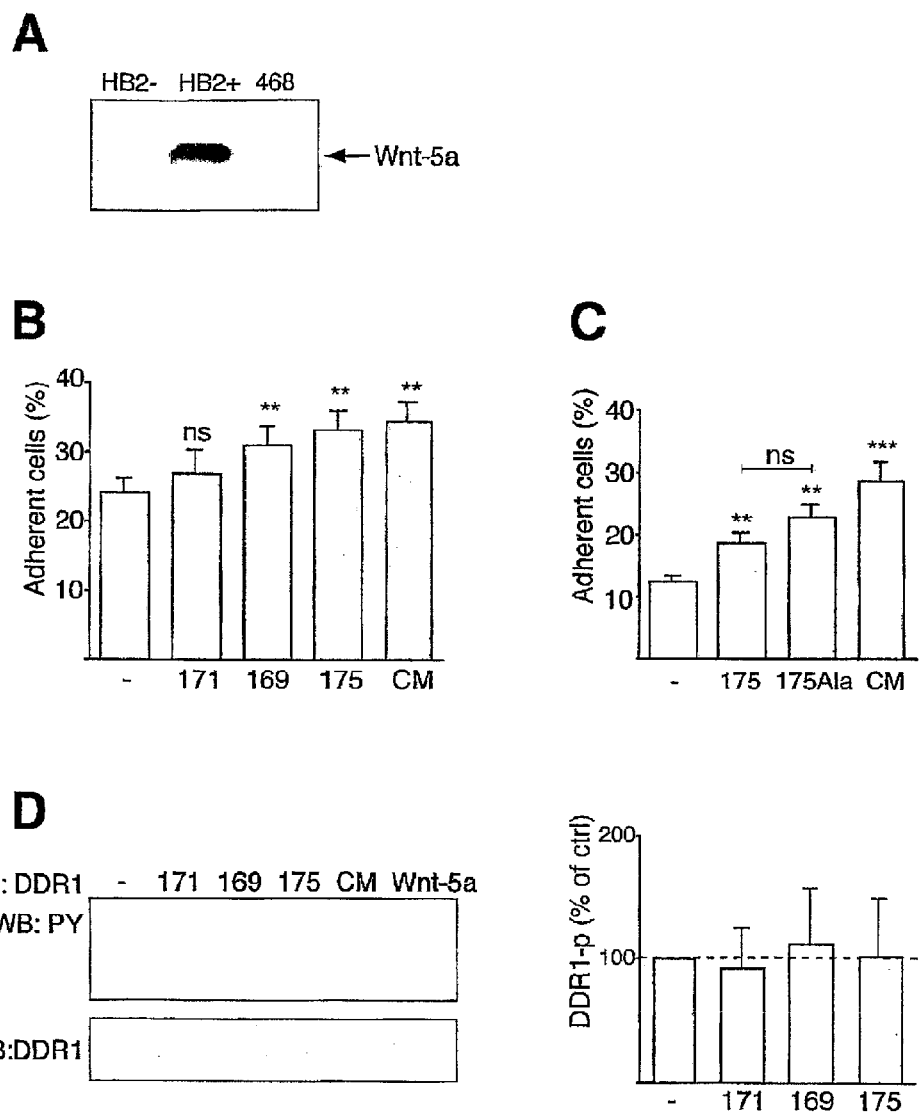
FIGS. 4A-4D illustrate the peptide-induced effects on adhesion and DDR1 phosphorylation in MDA-MB-468 breast cancer cells.

Based on the interest in re-constituting Wnt-5a signaling in breast cancer cells and thereby potentially impair their metastatic capacity, the effects of the pure peptides 169, 175 and the control peptide 171 was investigated next on adhesion of Wnt-5a lacking human MDA-MB-468 breast cancer cells to collagen I. The level of Wnt-5a protein expression in MDA-MB-468 cells was first analyzed in relation to both Wnt-5a antisense and HA-Wnt-5a over-expressing HB2 cells. As seen in FIG. 4A, both Wnt-5a antisense HB2 cells and MDA-MB-468 cells have low protein levels of Wnt-5a whereas Wnt-5a transfected cells express a very high level of the Wnt-5a protein. The expression of Wnt-5a is known to depend on culturing conditions and also on how confluent the cells are at the time of analysis (23). Consequently, the cells analyzed in FIG. 4A were harvested under the same conditions as in the later experiments, i.e., at 80-90% confluence and after being treated with serum-free medium for 16 h prior to each experiment unless otherwise stated.

The adhesion of MDA-MB-468 cells to collagen I was significantly increased in the presence of peptides 169 and 175 and by Wnt-5a containing CM, but not by the control peptide 171 (FIG. 4B). Peptides containing one or more free cysteines, such as peptide 175, may have unspecific effects by forming cysteine-cysteine interactions with different proteins/peptides. To investigate if the effect of peptide 175 on cell adhesion was related to its cysteine residue the effects of the cysteine containing peptide 175 with that of a peptide identical to the 175 peptide with the exception that the cysteine had been replaced with an alanine residue were compared. It was found that the alanine containing 175 was as effective in increasing adhesion as the cysteine-containing 175 and no statistical significant difference was observed between the cysteine containing and the alanine containing 175 peptides (FIG. 4C).

Figure 5:
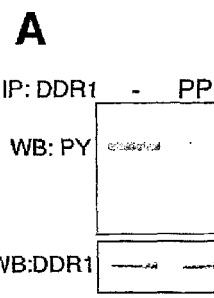
FIGS. 5A-5C illustrate the effects of DDR1 phosphorylation, SRC activity, and EGF activities in MDA-MB-468 cells.
Figure 5:
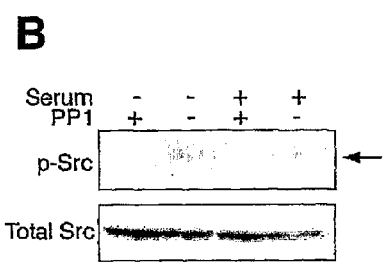
Figure 5:
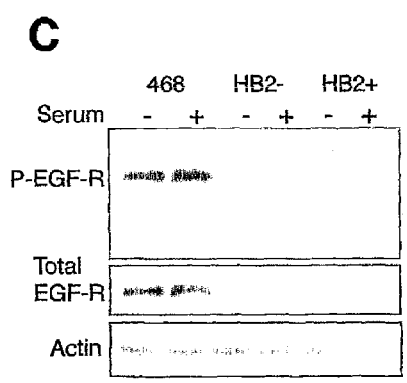

An interesting observation in the MDA-MB-468 cells is the constant, although modest, phosphorylation level of DDR1 seen even in the basal situation where no Wnt-5a or peptide is present (FIG. 4D). Furthermore, neither the pure peptides, CM nor recombinant Wnt-5a were able to further increase the level of DDR1 phosphorylation in the MDA-MB 468 cells (FIG. 4D). It has previously been shown that the Wnt-5a-dependent collagen-induced phosphorylation of DDR1 in MCF-7 and HB2 cells is mediated via a Src kinase (12). Consequently, the MDA-MB-468 cells were treated with 10 µM of the Src inhibitor 4-amino-5-(4-methyl-phenyl)-7-(t-butyl)pyrozolo-D-3,4-pyrimidine (PP1) for 30 min. Clearly, this treatment abolished the basal phosphorylation of DDR1 (FIG. 5A). This observation nicely correlates to the previously reported high Src kinase activity in MDA-MB-468 (24), here confirmed and shown to be independent of the presence of serum but abolished by PP1 (FIG. 5B). It has been suggested that the elevated Src activity in these cells is due to over-expression and hyperactivity of EGF-receptors (25). In line with this, the EGF-receptor is abundantly expressed and highly phosphorylated in MDA-MB-468 cells even after serum-starvation for 16 h (FIG. 5C). Possibly this hyperactivity of the EGF-receptors and the resulting high Src activity is the underlying cause of the constant DDR1 phosphorylation observed in MDA-MB-468 cells. Although these findings are not directly related to the present effort to identify Wnt-5a mimicking peptides they clearly reveal that i/enabling DDR1 activation is not the only means by which Wnt-5a affects mammary cell adhesion and motility and ii/other mechanisms apart from Wnt-5a signaling can via Src activation enable collagen-induced DDR1 activation.

Figure 6:
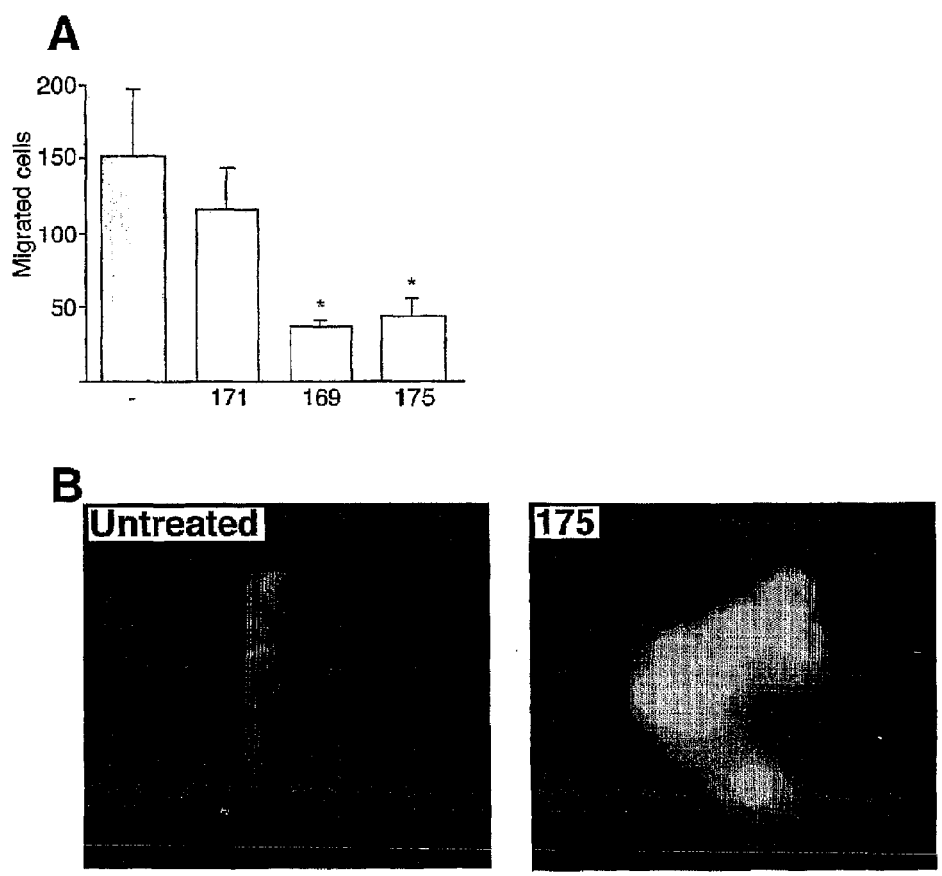
FIGS. 6A and 6B illustrate the peptide-induced effects on MDA-MB-468 tumour cell migration and their content of F-actin.

It is known that migration is a prerequisite for cancer invasion and metastasis and that increased cell migration in a Boyden chamber systems correlates with increased invasive properties of tumour cells in vivo. Therefore the effects of the pure peptides 171 (control), 169 and 175 were investigated on MDA-MB-468 cell motility in a Boyden chamber assay Both peptide 169 and 175 significantly decreased the migration of MDA-MB-468 cells, whereas the control peptide 171 had no statistically significant effect (FIG. 6A). The same results were obtained if the wells and the membranes were coated with collagen I (10 µg/ml) at 37° C. for 1 h prior to the initiation of the experiments (data not shown). En passant, it was observed that MDA-MB-468 cells exposed to peptide 175 had a significantly higher cellular content of filamentous actin (F-actin) as compared to untreated cells, here visualized by staining with AlexaFluor® 488 phalloidin (FIG. 6B). In the absence of an increased DDR1 activation, this increase in F-actin could well explain the peptide-induced increase in adhesion and impaired motility of MDA-MB-468 cells, since an increased F-actin content is known to render a cell more rigid and thus less motile.

Effects of sequential deletion of amino acids and formylation on the 175 peptide-induced effects on adhesion and migration of MDA-MB-468 tumour cells.

Figure 7:
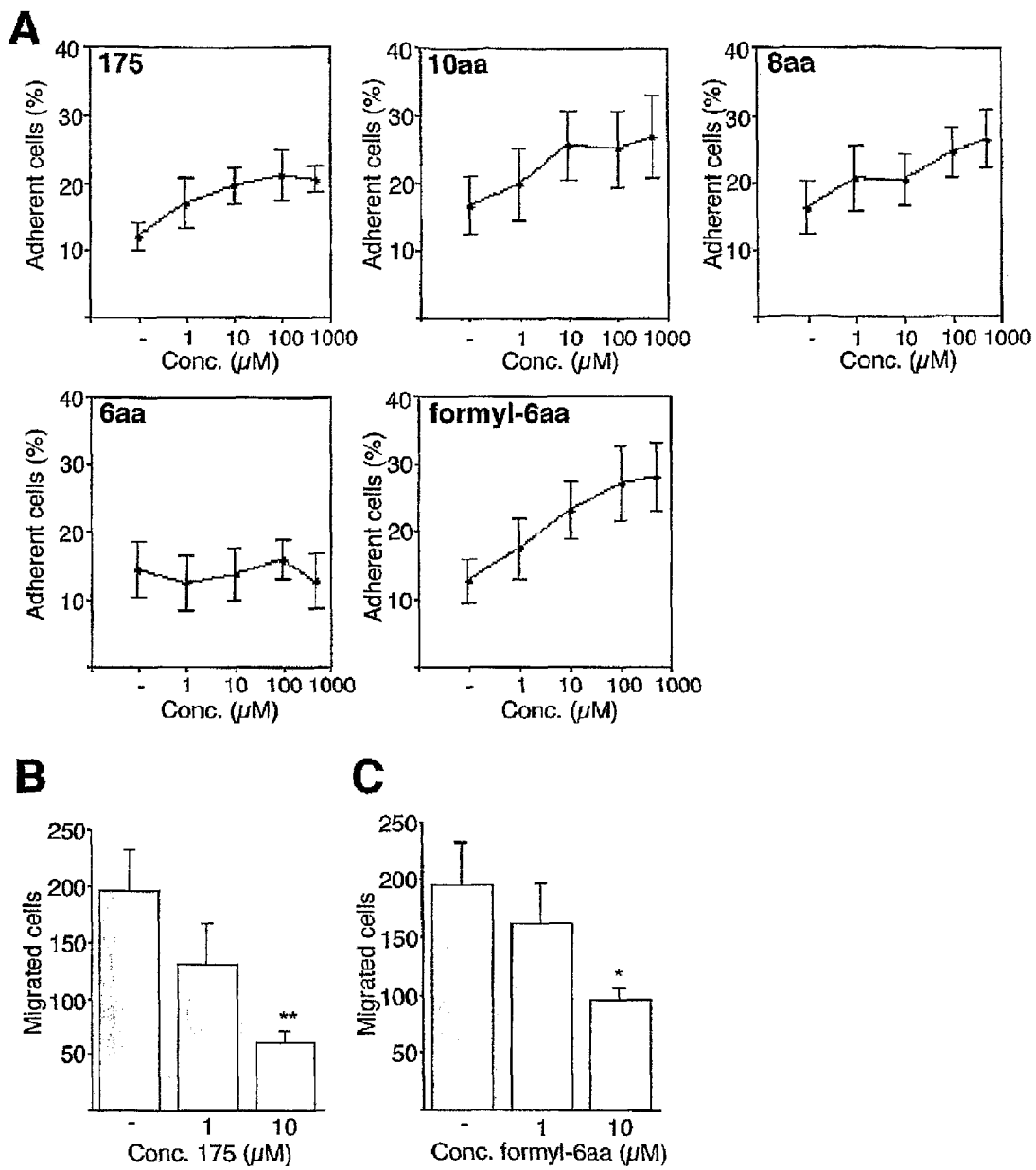
FIGS. 7A-7C illustrate the effects of peptide 175 modifications on its ability to induce MDA-MB-468 tumour cell adhesion and migration.

To identify the shortest possible peptide that still had adhesive and anti-motile effects, sequential deletions of two amino acids from the N-terminal side of the shorter of the two identified active peptides that is the 175 peptide, was performed. The effect on tumour cell adhesion was gradually lost when 2 amino acids at a time were removed from the peptide 175, and when only 6 amino acids remained no effect was detectable (FIG. 7A). It is well known that N-formylated peptide ligands from bacteria can potently activate leukocytes by binding to G-protein-coupled receptors on these cells. In this context the formyl group increases the effect of the ligand by 3 or 4 orders of magnitude. Interestingly enough, such bacterial peptides and Wnt-5a bind G-protein-coupled receptors and some of these bacterial peptides and our hexapeptide have a methionine residue in their N-terminal. Accordingly, we tested the effect of a formylated variant of our hexapeptide on cell adhesion. Formylation of the N-terminal methionine of this hexapeptide restored, and possibly even potentiated its effect on adhesion (FIG. 7A). Control experiments revealed that the formylated tripeptide fMet-Leu-Phe, known to activate leukocytes (19) did not affect MDA-MB-468 cell adhesion (control 15.3±3.6, fMet-Leu-Phe 15.7±4.5; n=6). This indicates a specific role of the Wnt-5a hexapeptide sequence in mediating the effect of the formylated hexapeptide. In accordance with the effects of the formylated hexapeptide and the peptide 175 on cell adhesion it could be also shown that at a concentration as low as 10 µM, both peptides significantly impaired the motility of MDA-MB-468 cells (FIGS. 7B and 7C).

Figure 8:
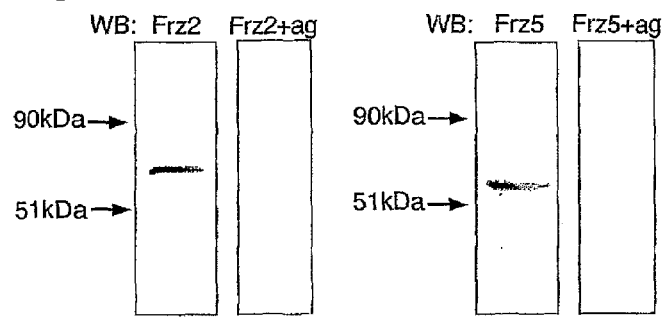
FIGS. 8A-8C illustrate the effects of Frz-5 receptor blocking and reduced pH on the abilities of the formylated hexapeptide and Wnt-5a to inhibit tumour cell migration.
Figure 8:
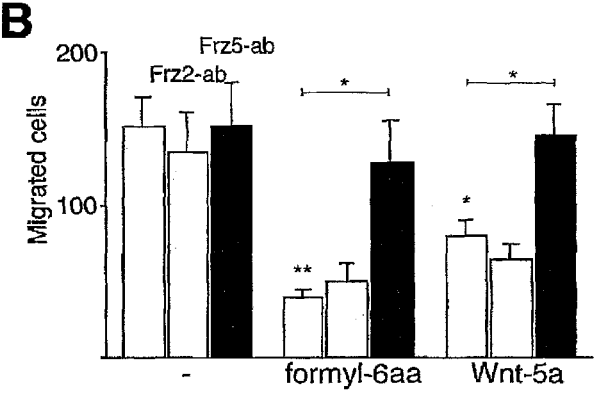
Figure 8:
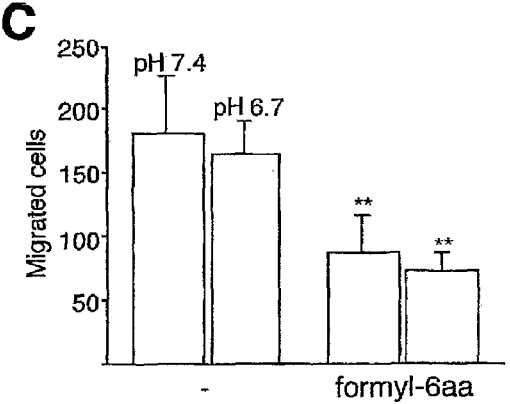

To ensure that the formylated hexapeptide and recombinant Wnt-5a are actually ligands binding to the Frz-5 receptor in mammary cells, as previously shown in synoviocytes and malignant melanoma cells, the previously described blocking Ab for the Frz-5 receptor was generated and a control Ab raised against the same sequence in the ectodomain of the Frz-2 receptor. The blots in FIG. 8A show that these two affinity purified Ab specifically recognize protein bands that perfectly matches the molecular weight of the Frz-2 and the Frz-5 receptor, respectively. Peptide-blocking experiments in which the Ab were preincubated with the antigen peptides to which they were raised (1:10 molar ratio) were also performed. In the subsequent Western blot analysis the detection of the Frz-2 and Frz-5 receptors were undetectable even if the films were heavily overexposed (FIG. 8A, lanes 2 and 4, respectively). In agreement with previous data from malignant melanoma (14) the Wnt-5a-induced decrease in MDA-MB-468 cell migration could be shown to be mediated via the Frz-5 receptor, whereas the control anti-Frz-2 Ab had no effect (FIG. 8B). Interestingly enough, it could also be demonstrate that the effect of the formylated hexapeptide on MDA-MB-468 cell migration is mediated via the Frz-5 receptor (FIG. 8B). In the context of inhibiting tumour cell migration in vivo one has to remember that the pH to be encountered in breast tumour tissue is approximately 6.7. Consequently, it was intriguing to observe that the formylated hexapeptide is as effective in inhibiting MDA-MB-468 cell migration at pH 6.7 as at pH 7.4 (FIG. 8C).

In the present investigation different peptides from the Wnt-5a protein sequence were generated and two of these that had Wnt-5a mimicking capabilities in terms of inhibition of breast cancer cell motility were identified. It was reasoned that the Wnt-5a was likely to interact, like many other protein ligands, with its receptor through at least one solvent exposed loop at its surface. Since the experimental three-dimensional structure of Wnt-5a is unknown, homology modeling methods could not be applied due to the lack of appropriate template. As such, in order to predict which segment of Wnt-5a could form a solvent exposed loop, secondary/solvent accessible surface predictions with PHD were performed. The results (reported in Table 1) allowed us to initially focus the study on only a few 8 to 15 amino acid long peptides.

Previously several peptide ligands have successfully been identified, among these the well-established tripeptide Arg-Gly-Asp, which functions as an integrin receptor ligand and the two hexapeptides that specifically can activate the G-protein-coupled protease-activated receptors 1 and 4 (18). Another example, but this time with an antagonizing effect, is the septapeptide that binds the G-protein coupled thrombin (30). In this study peptide-induced effects on mammary cell adhesion were used as the primary screening approach. By this tactic two peptides were identified that at high purity (95%) increased the adhesion to collagen I in a concentration-dependent manner in both non-cancerous HB2 cells and MDA-MB-468 cancer cells (cell lines with very low endogenous levels of the Wnt-5a protein). To identify the shortest possible peptide that still had an anti-motile effect similar to that of Wnt-5a, sequential deletions of two amino acids from the N-terminal side of the shorter of these two peptides (twelve amino acids long) were performed. It was found that the octapeptide still had adhesion-increasing effects, whereas the hexapeptide had none. However, the fact that the N-terminal amino acid on this hexapeptide was a methionine, which brought to mind the strong promoting effect that is exerted by the formyl group of the N-terminal methionin of the bacteria-derived fMet-Leu-Phe peptide (19, 31-33). N-formylated methionine is the initiating amino acid in the synthesis of all bacterial proteins. During an infection a large number of bacteria are disintegrated for various reasons and during this process there is a release of short N-formylated peptides from the bacteria. These peptides are very potent activators of leukocytes by their high affinity binding to the G-protein coupled formyl peptide receptors on these cells (31, 33).

The hexapeptide sequence Met-Asp-Gly-Cys-Glu-Leu (SEQ ID NO: 15) is unique for the Wnt-5 proteins in mammalian cells, but it is present in two different proteins in bacteria. However, in neither case has the hexapeptide sequence an N-terminal location and can thus not be present in a formylated state. Consequently, the presently described N-formylated hexapeptide is a unique peptide that can be found in neither bacteria nor mammalian cells. In this context it should be mentioned that N-formyl-Met-Leu-Phe, the potent tripeptide that activates leukocytes, had no effect on MDA-MB-468 cell adhesion, indicating that not just any formylated peptide will bind and activate the Frz-5 receptor on these cells.

It has previously been shown that a loss of Wnt-5a expression leads to a decreased breast tumour cell adhesion and thus an increased motility. These results taken together with the knowledge that increased cell migration is an underlying problem in cancer metastasis, made us eager to investigate an anti-motile effect of the formulated hexapeptide on breast tumour cells. These experiments were performed in a modified Boyden chamber, because the motile activity of tumour cells in such an assay has previously been shown to correlate well with their invasive behavior in vivo. In good agreement with the effect that the formylated hexapeptide had on MDA-MB-468 tumour cell adhesion it also strongly impaired their migration. It was thought that DDR1 is responsible for the effect on adhesion and migration. The fact that MDA-MB-468 cells exhibit a constant DDR1 phosphorylation in the absence or presence of peptides, CM or recombinant Wnt-5a indicate that Wnt-5a can act through an additional mechanism, through which it affects MDA-MB-468 tumour cell migration. The observation of a significant peptide-induced increase in F-actin in parallel with a decreased motility suggests that F-actin-mediated stiffness of the cells could be an alternative explanation for their stronger adhesion and reduced motility. The minimal concentration of the formylated hexapeptide that had a significant effect on migration was 10 µM, which is in good agreement with the finding by Andersen and co-workers, who found that the lowest functional concentrations of their hexapeptides in platelets were 10 µM.

The potential clinical significance of the present findings is obvious. The fact that lack of endogenous Wnt-5a protein expression in mammary tumour cells is strongly associated with a higher histological grade and a reduced disease free survival for these patients (9), indicating a need for a means to reconstitute Wnt-5a signaling in such tumour cells and thus delay or inhibit the formation of distal metastases. Furthermore, reconstitution of Wnt-5a signaling also appears to be a future therapeutic approach in other tumour forms, since Wnt-5a has been shown to have tumour suppressor activity in thyroid carcinoma and loss of Wnt-5a expression is associated with high-risk neuroblastoma.

Due to inefficient vascularization as well as an increased lactate production the extracellular pH in solid tumour tissue is lower than in normal tissue. However, in human breast tumours the $Na^+$—$H^+$ exchanger isoform 1 has also been suggested to participate in the regulation of both extracellular and intracellular pH. It is therefore of vital importance for any potential metastasis-inhibiting substance that it is effective also at the low pH encountered in the tumour tissue. Attempts to estimate the pH in solid tumour tissue in vivo have estimated it to be approximately 6.75. Interestingly enough, the present data show that the formylated hexapeptide which was identified inhibits MDA-MB-468 breast tumour cell motility as well at a low pH (6.7) as at a normal pH (7.4).

In conclusion it has been established that a novel formyl-Met-Asp-Gly-Cys-Glu-Leu (formylated SEQ ID NO: 15) peptide ligand derived from the Wnt-5a ligand has the potential to mimic the effects of the full Wnt-5a molecule in binding to the Frz-5 receptor and impairing the motile capacity of a human breast tumour cell line that has a low endogenous Wnt-5a protein expression. This peptide ligand can serve as a model substance for future development of an innovative anti-metastatic treatment for those patients (approximately 50%) that have been diagnosed with a breast cancer that exhibits a reduced endogenous expression of Wnt5a.

Methods

Cell Culture.

The HB2 mammary epithelial cell line, a subclone of the MTSV-1.7 cell line, originating from the laboratory of Dr. J. Taylor-Papadimitriou (11) was used. The HB2 cells were cultured in DMEM supplemented with 10% FBS, 5 U/ml penicillin, 0.5 U/ml streptomycin, 2 mM glutamine, 10 µg/ml bovine insulin and 5 µg/ml hydrocortisone. The human mammary carcinoma cell lines MCF-7 and MDA-MB-468 were cultured in DMEM supplemented with 10% FBS, 5 U/ml penicillin, 0.5 U/ml streptomycin and 2 mM glutamine. The pH-experiments were done in MEM supplemented with 10 mM Tris, 0.5% BSA, 5 U/ml penicillin, 0.5 U/ml streptomycin and 2 mM glutamine. The pH 7.4-medium was further supplemented with 4 mM sodium bicarbonate whereas the pH 6.7-medium was not. All cells were incubated at 37° C. in 95% air and 5% $CO_2$.

Chemicals and Reagents.

The sources of Ab and chemicals were as follows: anti-actin monoclonal Ab C4 (MP Biomedicals, Irvine, Calif.), anti-β1 integrin monoclonal Ab P5D2 (Chemicon, Temecula, Calif.), collagen, type I from rat tail and anti-EGF-receptor Ab (activated form) (BD Biosciences, San Jose, Calif.), anti-EGF-receptor Ab (all forms) and anti-phosphotyrosine monoclonal Ab 4G10 (Upstate Biotech. Inc. Lake Placid, N.Y.), PP1 (Biomol, Plymouth Meeting, Pa.), recombinant mouse Wnt-5a (R&D Systems, Abingdon, UK), anti-Src Ab (Santa Cruz, Santa Cruz, Calif.), anti-Src [$pY^{418}$] (Biosource Int, Camarillo, Calif.) and SDS-PAGE reagents (BioRad Laboratories, Hercules, Calif.).

Peptide Synthesis.

In most cases Eurogentec (Seraing, Belgium) synthesized the different peptide fragments derived from the Wnt-5a molecule. However, the shorter peptides and the formylated peptide derived from the 12 amino acid long 175 peptide were synthesized by Pepscan systems (Lelystad, Netherlands). All other laboratory reagents were obtained from Sigma Aldrich Corporation (St Louis, Mo.).

Receptor Blocking Antibodies.

The peptide CPILKESHPLYNKVRTGQVPN (SEQ ID NO: 28), corresponding to amino acids 198-217 in the ectodomain of the human Frz-5 receptor was as previously described used to generate a Frz-5 receptor blocking Ab (13). The peptide CPRVLKVPSYLSYKFLGERD (SEQ ID NO: 29), corresponding to amino acids 202-220 in the ectodomain of the human Frz-2 receptor, was used to generate a control anti-Frz-2 Ab. The synthesis of the peptides (the italic letters indicate the Frz-5 and Frz-2 sequences, the cysteine was added for raising and purifying the Ab) and the production of rabbit anti-Frz-5 and anti-Frz-2 antisera were managed by AgriSera (Vännäs, Sweden; permit A69-04 from Umeå animal ethic committee). The antisera were affinity purified in the laboratory by coupling the respective peptide antigen to Sulfolink Sepharose over which the respective antisera was then eluted.

Immunoprecipitation and Western Blot.

Western blot analysis was performed to evaluate the protein expressions of Wnt-5a, EGF-receptor, Src and Frz-2 and 5 in HB2 and MDA-MB-468 cells. Evidently the batch of MDA-MB-468 cells used in the present study had a low Wnt-5a expression level. The Wnt-5a Ab has been produced in the laboratory, as previously described (9, 10). The cells were lysed and boiled in two times concentrated Laemmli buffer. The protein content was determined in each sample and adjusted to ensure loading of equal amounts of protein in each lane, 50 mM DTT was then added and the lysates were boiled for 10 min, before separation by SDS gel electrophoresis. The proteins were subsequently transferred to PVDF membranes. The membranes were blocked in 3% BSA or 5% non-fat milk for 45 min, incubated with the primary Ab for 1 h (1:2,000 for Wnt-5a, 1:1,000 for activated EGF-receptor, total EGF-receptor, actin, active Src and total Src, and 1:5,000 for Frz-2 and Frz-5), and then for 1 h with a horseradish peroxidase conjugated secondary Ab. The Ab-antigen complex was detected using an enhanced chemiluminescence detection kit from Amersham Pharmacia Biotech (Uppsala, Sweden). In the case of re-probing, the membranes were stripped with a Reblot Strong solution from Chemicon International (Temecula, Calif.).

The phosphorylation status of DDR1 was analyzed as previously described (12), with the following modifications. After serum-depletion for 16 h, the cells were detached with Versene and then allowed to adhere to collagen I for 60 (MDA-MB-468) or 90 min (HB2) at 37° C. The experiments were terminated by lysing both adherent and non-adherent cells with a lysis buffer (50 mM Tris pH 7.4, 1% Triton-X, 5 mM EDTA, 5 mM EGTA, 50 mM NaCl, 10 µg/ml aprotinin, 2.5 mM benzamidine, 1 mM pefabloc, 1 µg/ml leupeptin and 1 mM $Na_3VO_4$). For immunoblotting an anti-DDR1 rabbit polyclonal Ab, sc-532 (Santa Cruz Biotech, Santa Cruz, Calif.) was used at a dilution of 1:10,000. The Ab recognizes DDR1b/c, which is essential because collagen only induces phosphorylation of the b or c isoforms of DDR1 in mammary epithelial cells (10).

Adhesion Assay.

The adhesion assay was carried out as previously described (12). Briefly, cells were serum-depleted for 16 h, detached with Versene and allowed to adhere as single cells to collagen I for 60 (MDA-MB-468) or 90 min (HB2) at 37° C. Non-adherent cells were removed by washing with PBS. The adherent cells were incubated with a (3-(4,5-dimethylthiazol-2-yl)-5-(3-carboxymethoxyphenyl)-24-4-sulfopheny-1-)-2H-tetrazolium, inner salt (MTS) dye reduction assay (Promega, Madison, Wis.) and absorbance was measured at 490 nm using a Fluostar microplate reader from BMG LabTechnologies (GmbH, Offenberg, Germany). In each experiment a single value was calculated based on the mean of adhesion from six separate wells after the adhesion to plastic alone had been subtracted. The CM used as a control in the adhesion assays was obtained from confluent Wnt-5a overexpressing HB2 cells (for experiments with Wnt-5a antisense HB2 cells) or Wnt-5a overexpressing MCF-7 cells (for MDA-MB-468 cells) stably transfected with a vector overexpressing Wnt5a. A collected CM was always used within three days.

Control of the CM.

To control the specificity of the CM, it was incubated with either the Wnt-5a or a control Ab for 45 min at 37° C. Subsequently 10 µl Protein A Sepharose was added for 30 min and after the protein A-bound antibodies were collected by centrifugation the remaining supernatants were used for the experiments.

Cell Migration Assay.

Cell migration analyses were performed in a modified Boyden chamber with a polycarbonate membrane (10 µm thick with a porous diameter of 8.0 µm) separating the two chambers (Transwell®; Costar, Cambridge, Mass.). As indicated in some experiments the membranes were coated with collagen by adding collagen-I (10 µg/ml) diluted in 0.25% acetic acid to the upper chamber for 1 h at 37° C., after which it was washed three times with PBS. Each experiment was initiated by detaching the cells by Versene treatment for 10-20 min at 37° C., washed, and re-suspended as a single cell suspension in serum-free DMEM medium supplemented with 0.5% BSA. Together with the indicated agonist a 0.2 ml cell suspension (containing 25,000 MDA-MB-468 or 50,000 HB2 cells) was then added to the upper chamber of the transwell. The lower chamber was filled with 0.6 ml serum-free but BSA-containing DMEM medium supplemented with 1 ng/ml of the chemoattractant IGF-I. As a control, IGF-I was excluded in some wells in each separate experiment. The cells were allowed to migrate in the Boyden chamber for 18 h at 37° C. in a humidified atmosphere of 95% air and 5% $CO_2$. The experiments were terminated by removing the non-migratory cells with a cotton-tipped applicator from the upper surface of the membranes. The remaining cells on the lower surface that had migrated through the membrane were stained for 20 min with 0.5% crystal violet diluted in 20% methanol/80% water. After washing the membranes the number of stained cells per membrane and well was counted in an inverted microscope. The value from each separate experiment represents the median value of three individual wells.

Fluorescent Microscopy.

MDA-MB-468 cells were detached from the tissue culture dishes by incubation with Versene for 10 min at 37° C., washed, re-suspended as single cells in serum-free DMEM medium supplemented with 0.5% BSA with or without peptide 175 (100 µM), and plated on a cover glass, pre-coated with 10 µg/ml collagen-I, in a cell culture dish. These experiments were terminated after 18 h by fixing the cells with 4% paraformaldehyde for 10 min at 4° C.

The cells were then permeabilized by incubation with 0.5% Triton X-100 for 5 min and blocked by incubation with a 3% BSA solution supplemented with 0.3% Triton X-100 for 45 min. The staining of the cells was performed in the dark by incubation for 40 min with AlexaFluor® 488 phalloidin (Molecular Probes, Eugene, Oreg.) at a dilution of 1:500 and in the presence of 1% BSA. Thereafter the cells were extensively washed and finally mounted with Dako Cytomation fluorescent mounting medium. The samples were examined and photographed in a Nikon Eclipse 800 microscope using a 60×oil immersion objective.

Pharmaceutical Formulations

When employed as pharmaceuticals, the compounds of this invention are usually administered in the form of pharmaceutical compositions. These compounds can be administered by a variety of routes including oral, and rectal. These compounds are effective as oral compositions. Such compositions are prepared in a manner well known in the pharmaceutical art and comprise at least one active compound.

This invention also includes pharmaceutical compositions, which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatine capsules, suppositories, and packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatine, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propyl hydroxy-benzoates; sweetening agents; and flavouring agents. The compositions of the invention can be formulated so as to provide quick, sustained or delayed release of the active ingredient after administration to the patient by employing procedures known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of Formula (I) above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. For example, when the drug is administered via the oral route, each dosage contains from about 1 mg to about 1000 mg, preferably about 2 mg to about 500 mg, more preferably about 5 mg to about 100 mg, even more preferably about 5 mg to about 60 mg, of the active ingredient. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patent's symptoms, and the like. From a principle point of view the formulation should be administered simultaneously with a food intake, and should then be administered in an amount providing a sufficient inhibition of lipids. Thus the body may need some lipids from a nutritional point of view and this may then influence the amount of inhibiting compounds of the invention administered. The effect of the compounds of the invention takes place in the small intestine and thus there is no further effect obtained as such, but of possible metabolites of the compounds.

For preparing solid compositions such as tablets, the principal active ingredient is mixed with a pharmaceutical excipient to form a solid preformulation composition containing a homogeneous mixture of a compound of the present invention. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation is then subdivided into unit dosage forms of the type described above containing the active ingredient of the present invention.

The tablets, pills or granules of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The tablets, pills or granules of the present invention may be coated with a sustained release coating enabling release at pancreas, where the pancreatic lipase is set free to the intestine. Such a sustained release coating will thus allow for a small release, if any, in the stomach, but allow for total release in the upper part of the small intestine.

For example, a tablet may be prepared by compression or moulding. Compressed tablets may be prepared by compressing in a suitable machine a composition of the invention in a free-flowing form such as powder or granules, optionally mixed with a binder, a lubricant, an inert diluent, and/or a surface active or dispersing agent. Moulded tablets may be made by moulding in a suitable machine, a mixture of the powdered compound moistened with an inert liquid diluent.

In a preferred embodiment, at least one pharmaceutically acceptable excipient is a binder, a filler, or a mixture thereof. Suitable excipients include lubricants, disintegrants, and mixtures thereof. Preferred excipients include, but are not limited to, lactose, croscarmellose, microcrystalline cellulose, pre-gelatinised starch, and magnesium stearate.

Binders suitable for preparing dosage formulations of the pharmaceutical compositions of the invention include, but are not limited to, corn starch, potato starch, or other starches, gelatine, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinised starch, hydroxypropyl methyl cellulose, (e.g., Nos. 2208, 2906, 2910), microcrystalline cellulose and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, of Marcus Hook, Pa.). A particularly suitable binder is a mixture of microcrystalline cellulose and sodium carboxymethyl cellulose sold as AVICEL RC-581 by FMC Corporation.

Examples of suitable fillers for use with the dosage forms of the compounds of the invention include, but are not limited to, talc, calcium carbonate (e.g., granules or powder), microcrystalline cellulose, powdered cellulose, dextrates, kaolin, mannitol, salicylic acid, sorbitol, starch, pre-gelatinised starch, and mixtures thereof.

Typically, from about 50 to about 99 weight percent of a solid dosage form of the invention is binder and/or filler.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the compound of the invention from the dosage form. Thus, a sufficient amount of disintegrant that is neither too little nor too much to detrimentally alter the release of the drug should be used to form solid dosage forms of the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, may be used in the pharmaceutical composition. Suitable disintegrants that may be used to form solid dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pregelatinised starch, other starches, clays, other algins, other celluloses, gums and mixtures thereof.

Suitable lubricants for use with solid dosage forms include, but are not limited to, calcium stearate, magnesium stearate, mineral oil, light mineral oil, glycerine, sorbitol, mannitol, polyethylene glycol, other glycols, stearic acid, sodium lauryl sulphate, talc, hydrogenated vegetable oil (e.g., peanut oil, cottonseed oil, sunflower oil, sesame oil, alive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. A lubricant may optionally be added, typically in an amount of less than about 1 weight percent of the pharmaceutical composition.

Preferably, each solid dosage form contains from about 5 mg to about 3000 mg of the compound of the invention. Preferably, each solid dosage form contains about 5 mg, about 25 mg, about 100 mg, about 200 mg, about 250 mg, or about 500 mg of the compound of the invention. Solid dosage forms suitable for oral administration preferably contain from about 5 mg to about 200 mg the compound of the invention.

The liquid forms in which the novel compositions of the present invention may be incorporated for administration orally include aqueous solutions, suitably flavoured syrups, aqueous, and flavoured emulsions with edible oils such as corn oil, cottonseed oil, sesame oil, coconut oil, or peanut oil, as well as elixirs and similar pharmaceutical vehicles.

Furthermore, the pharmaceutical compositions containing one or more compound(s) of this invention can be administered in combination any other suitable drug, for example for the treatment of gastrointestinal disorders. When the combination therapy is employed, the pharmaceutical composition containing the compound(s) of this invention and the second drug may be administered simultaneously, sequentially or separately. Each component used in the combination therapy is employed in an amount sufficient for its intended purpose. For example, the secondary drug is employed in sufficient amounts to effect reduction of symptom in question in vivo.

Preferably, the dose range for compounds of this invention is from about 1 mg to about 1000 mg per dose, more preferably about 2 mg to about 500 mg, even more preferably about 5 mg to about 100 mg, and still more preferably about 5 mg to about 60 mg. Again, the particular dose used will depend on the patient (age, weight, etc.), and the severity of the disease (mild, moderate, severe). Lastly, a pharmaceutical composition containing two active ingredients can also be prepared for administering the drugs simultaneously.

The administration of the present drug(-s) will normally take place in connection with food intake, when lipase-colipase are set free due to digestion and an optimal inhibition will be obtained below duodenum.

EXAMPLES

The following preparations and examples are given to enable those skilled in the art to more clearly understand and to practice the present invention. They should not be considered as limiting the scope of the invention, but merely as being illustrative and representative thereof.

Formulation Examples

Example 1

Hard gelatine capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatine capsules in 340 mg quantities.

Example 2

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120.0 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50 to 60° C., and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 4

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatine capsules in 150 mg quantities.

Example 5

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mould of nominal 2.0 g capacity and allowed to cool.

Example 6

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavour and Colour | q.s. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavour, and colour are diluted with some of the water and added with stirring. Sufficient water is then added to produce the required volume.

Example 7

A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatine capsules in 425.0 mg quantities. Other suitable formulations for use in the present invention can be found in Remington's Pharmaceutical Sciences, edited by E. W. Martin (Mack Publishing Company, 18th ed., 1990).

FIGURE LEGENDS

FIG. 1

Effects of crude peptides on collagen-induced DDR1 phosphorylation in Wnt-5a antisense HB2 cells. Single cells were allowed to adhere to collagen I-coated plates in the presence of the indicated crude peptide (100 μM). (A) Experiments performed in the presence of peptides 167-173. (B) Experiments performed in the presence of peptides 175-180. After 90 min the cells were lysed and DDR1 immunoprecipitated. Subsequently, the immunoprecipitates were subjected to Western blot analysis with an anti-phosphotyrosine Ab and then, after stripping, with an anti-DDR1 Ab to ascertain equal loading. The blots shown are representative of 3 separate experiments. The diagrams show densitometric analysis of DDR1 phosphorylation, expressed as percent of control.

FIG. 2

Effects of crude peptides on adhesion of Wnt-5a antisense HB2 cells to collagen. (A) Single cells were allowed to adhere for 90 min in the absence or presence of the indicated crude peptides (100 μM). The amounts of adhesive cells were analyzed as described in the methods and the results are given as means±SEM of 7 separate experiments. (B) Adhesion of Wnt-5a antisense HB2 cells to collagen was analyzed after pre-treating the cells with an anti-β1-integrin Ab for 45 min before letting them adhere for 90 min in the absence or presence of peptides 171 or 175 (100 μM) or CM. The amounts of adhesive cells were analyzed as described in the methods and the results are given as means±SEM of 6 separate experiments (C) The diagram outlines a control of the presently used CM. The cells were allowed to adhere to collagen I-coated wells in the absence or presence of normal CM or Wnt-5a depleted CM. The amounts of adhesive cells were analyzed as described in the methods and the results are given as means±SEM of 6 separate experiments. Ns=not significant, * $p<0.05$,  $p<0.01$ and * $p<0.001$.

FIG. 3

Effects of the selected and pure peptides on the ability of Wnt-5a antisense HB2 cells to adhere and migrate. (A-E) The ability of the cells to adhere to collagen type I-coated wells was analyzed as previously described for FIG. 2 in the absence or presence of different concentrations of the indicated peptide. (F) Effect of the indicated peptides on migration of Wnt-5a antisense HB2 in a transwell migration assay. The cells were allowed to migrate for 18 h in the absence or presence of 100 μM peptide or 0.4 μg/ml of recombinant

FIG. 4

Peptide-induced effects on adhesion and DDR1 phosphorylation in MDA-MB-468 breast cancer cells. (A) Western blot analysis of Wnt-5a protein expression in Wnt-5a antisense and Wnt-5a over-expressing HB2 cells in comparison to MDA-MB-468 tumour cells. The blot is representative of 9 separate experiments. (B) Peptide-induced effects on MDA-MB-468 tumour cell adhesion. The cells were allowed to adhere to collagen type I-coated wells for 60 min in the absence or presence of 100 μM of the indicated peptides or CM. The amounts of adhesive cells were analyzed as described in the methods and the results are given as means±SEM of 8 separate experiments. (C) MDA-MB-468 cell adhesion to collagen I-coated wells in the absence or presence of peptide 175 or a peptide with same amino acid sequence except for a substitution of cysteine for alanine (175Ala) or CM. The amount of adherent cells was estimated as in panel A and expressed as means±SEM of 6 separate experiments, ns=not significant,  $p<0.01$ and * $p<0.001$. (D) Single MDA-MB-468 cells were allowed to adhere to collagen I-coated plates for 60 min in the absence or presence of the indicated peptides (100 μM), CM or recombinant Wnt-5a (0.8 μg/ml). DDR1 immunoprecipitates were Western blotted with first an anti-phosphotyrosine Ab and then after stripping with an anti-DDR1 Ab. The blots shown are representative of 6 separate experiments. The diagram to the right shows a densitometric analysis of the DDR1 phosphorylation data, expressed as percent of control.

FIG. 5

(A) Effect of pre-treatment (30 min) with the Src-inhibitor PP1 (10 μM) on adhesion induced DDR1 phosphorylation in MDA-MB-468 cells. The blots shown are representative of 3 separate experiments. (B) Src activity in MDA-MB-468 cells in the absence and presence of PP1 and/or serum. The cells were depleted or not with serum for 16 h and then treated or not with 10 μM PP1 for the last 30 min of this incubation period. The blots shown are representative of 6 separate experiments. (C) EGF receptor activities and expression levels in MDA-MB-468 cells and in Wnt-5a antisense or over-expressing HB2 cells. The blots shown are representative of 5 separate experiments.

FIG. 6

Peptide-induced effects on MDA-MB-468 tumour cell migration and their content of F-actin. (A) The cells were allowed to migrate for 18 h in the absence or presence of the indicated peptides (100 μM) The data in panel A are expressed as means±SEM of 8 separate experiments, each performed in triplicate. * $p<0.05$. (B) The cells were allowed to adhere to collagen I-coated cover glasses for 18 h in the absence or presence of peptide 175 (100 μM). The cells were then stained with Alexa488-Phalloidin as described in the methods section. The illustrated micrographs are representative of 5 separate experiments.

FIG. 7

Effects of peptide 175 modifications on its ability to induce MDA-MB-468 tumour cell adhesion and migration. (A) The cells were allowed to adhere for 60 min to collagen-I coated wells in the absence or presence of peptide 175, three stepwise N-terminal deletion variants of peptide 175 or a formylated version of the tested hexapeptide derived from peptide 175. The amounts of adhesive cells were analyzed as described in the methods and the results are given as means±SEM of 6 separate experiments. (B and C) The cells were allowed to migrate for 18 h in the absence or presence of 1 or 10 μM of peptide 175 (B) or the formylated hexapeptide (C). The data are given as means±SEM of 6 separate experiments, each performed in triplicate. * $p<0.05$, $p<0.01$.

FIG. 8

Effects of Frz-5 receptor blocking and reduced pH on the abilities of the formylated hexapeptide and Wnt-5a to inhibit tumour cell migration. (A) Western blot analysis of MDA-MB-468 cell lysates with the anti-Frz-2 and anti-Frz-5 Ab. Peptide (antigen)-blocking experiments revealed no detectable protein bands even after overexposure of the films. The blots are representative of 3 separate experiments. (B) Effects of anti-Frz-2 and anti-Frz-5 Ab on MDA-MB-468 cell migration. The cells were allowed to migrate for 18 h in the absence or presence of anti-Frz-2 or anti-Frz-5 Ab (5 μg/ml), grey and white bars respectively. As indicated the formylated hexapeptide (100 μM) or recombinant Wnt-5a (0.4 μg/ml) was added to the cells during the entire period of their migration. The data are given as means±SEM of 7 separate experiments, each performed in triplicate. (C) The MDA-MB-468 cells were allowed to migrate for 18 h in the absence or presence of the formylated hexapeptide (10 μM) in a media that had a pH of 7.4 (grey bars) or 6.7 (white bars). The data are given as means±SD of 4 separate experiments, each performed in triplicate. * $p<0.05$, ** $p<0.01$.

What is now claimed:

1. An isolated peptide selected from the group consisting of:

```
LGTQGRLCNKTSEGMDGCEL    SEQ. ID. NO. 1,
GTQGRLCNKTSEGMDGCEL     SEQ. ID. NO. 2,
TQGRLCNKTSEGMDGCEL      SEQ. ID. NO. 3,
QGRLCNKTSEGMDGCEL       SEQ. ID. NO. 4,
GRLCNKTSEGMDGCEL        SEQ. ID. NO. 5,
RLCNKTSEGMDGCEL         SEQ. ID. NO. 6,
LCNKTSEGMDGCEL          SEQ. ID. NO. 7,
CNKTSEGMDGCEL           SEQ. ID. NO. 8,
NKTSEGMDGCEL            SEQ. ID. NO. 9,
KTSEGMDGCEL             SEQ. ID. NO. 10,
TSEGMDGCEL              SEQ. ID. NO. 11,
SEGMDGCEL               SEQ. ID. NO. 12,
EGMDGCEL                SEQ. ID. NO. 13,
GMDGCEL                 SEQ. ID. NO. 14,
and
MDGCEL                  SEQ. ID. NO. 15.
```

2. A peptide according to claim 1, wherein the peptide is formylated.

3. A peptide according to claim 1, said peptide being MDGCEL (SEQ ID NO: 15).

4. A peptide according to claim 3, wherein the peptide is formylated.

5. A pharmaceutical composition containing a peptide selected from the group consisting of:

```
LGTQGRLCNKTSEGMDGCEL    SEQ. ID. NO. 1,
GTQGRLCNKTSEGMDGCEL     SEQ. ID. NO. 2,
TQGRLCNKTSEGMDGCEL      SEQ. ID. NO. 3,
QGRLCNKTSEGMDGCEL       SEQ. ID. NO. 4
GRLCNKTSEGMDGCEL        SEQ. ID. NO. 5,
RLCNKTSEGMDGCEL         SEQ. ID. NO. 6,
LCNKTSEGMDGCEL          SEQ. ID. NO. 7,
CNKTSEGMDGCEL           SEQ. ID. NO. 8,
NKTSEGMDGCEL            SEQ. ID. NO. 9,
KTSEGMDGCEL             SEQ. ID. NO. 10,
TSEGMDGCEL              SEQ. ID. NO. 11,
SEGMDGCEL               SEQ. ID. NO. 12,
EGMDGCEL                SEQ. ID. NO. 13,
GMDGCEL                 SEQ. ID. NO. 14,
and
MDGCEL                  SEQ. ID. NO. 15.
``` and a pharmaceutically acceptable inert carrier or excipient.

6. A pharmaceutical composition according to claim 5, wherein the peptide is formylated.

7. A pharmaceutical composition according to claim 5, wherein the peptide is selected from the group consisting of

```
NKTSEGMDGCEL            SEQ. ID. NO. 9,
KTSEGMDGCEL             SEQ. ID. NO. 10,
TSEGMDGCEL              SEQ. ID. NO. 11,
SEGMDGCEL               SEQ. ID. NO. 12,
EGMDGCEL                SEQ. ID. NO. 13,
GMDGCEL                 SEQ. ID. NO. 14,
and
MDGCEL                  SEQ. ID. NO. 15.
```

8. A pharmaceutical composition according to claim 7, wherein the peptide is formylated.

9. A pharmaceutical composition of claim 8, wherein the peptide is formylated MDGCEL (SEQ ID NO: 15).

10. An isolated peptide, wherein said peptide is a modification of:

```
NKTSEGMDGCEL            SEQ. ID. NO. 9,
``` wherein the cysteine positioned between the glycine and the glutamic acid has been replaced with alanine.

11. A peptide according to claim 10, wherein the peptide is formylated.

12. A pharmaceutical composition containing a peptide, wherein said peptide is a modification of: NKTSEGMDGCEL SEQ. ID. NO. 9, wherein the cysteine positioned between the glycine and the glutamic acid has been replaced with alanine, and a pharmaceutically acceptable inert carrier or excipient.

13. A pharmaceutical composition according to claim 12, wherein the peptide is formylated.

\* \* \* \* \*